United States Patent

Atkinson et al.

[11] Patent Number: 5,800,568
[45] Date of Patent: Sep. 1, 1998

[54] PROSTHETIC ANKLE AND WALKING SYSTEM

[75] Inventors: Stewart L. Atkinson; Donald L. Poggi, both of Bainbridge Island, Wash.

[73] Assignee: Model & Instrument Development Corporation, Poulsbo, Wash.

[21] Appl. No.: 602,241

[22] Filed: Feb. 16, 1996

[51] Int. Cl.$^6$ ............................................. A61F 2/66
[52] U.S. Cl. ............................................. 623/52; 623/55
[58] Field of Search ............................... 623/47, 50–53, 623/54, 55

[56] References Cited

U.S. PATENT DOCUMENTS

| | | | |
|---|---|---|---|
| 2,453,969 | 11/1948 | Carter | 623/53 X |
| 5,062,859 | 11/1991 | Naeder | 623/55 |
| 5,112,356 | 5/1992 | Harris et al. | 623/49 |
| 5,116,385 | 5/1992 | Allard et al. | 623/55 |
| 5,139,525 | 8/1992 | Kristinsson | 623/55 |
| 5,156,632 | 10/1992 | Wellershaus | 623/55 |
| 5,217,500 | 6/1993 | Phillips | 623/38 |
| 5,376,139 | 12/1994 | Pitkin | 623/51 |
| 5,425,781 | 6/1995 | Allard et al. | 623/38 |
| 5,458,656 | 10/1995 | Phillips | 623/27 |
| 5,653,767 | 8/1997 | Allen et al. | 623/52 |
| 5,653,768 | 8/1997 | Kania | 623/55 |

FOREIGN PATENT DOCUMENTS

| | | | |
|---|---|---|---|
| 2698538 | 6/1994 | France | 623/55 |
| 4037928 | 5/1992 | Germany | 623/55 |

*Primary Examiner*—David H. Willse
*Attorney, Agent, or Firm*—Seed and Berry LLP

[57] ABSTRACT

An inventive prosthetic ankle for use between a pylon and a prosthetic foot to support a person's weight on the ground comprises an integrally formed, generally C-shaped carbon-fiber composite flexure member having upper, lower and curved legs. The upper leg is connected to a lower end of the pylon, and the lower leg is connected to an upper surface of the prosthetic foot. The curved leg interconnects the upper and lower legs, with the curved leg extending from a forward edge of the upper leg to a forward edge of the lower leg in a rearwardly-facing arc about a medial/lateral axis positioned forward of the pylon. The curved leg is dog-boned to facilitate canting of the pylon with respect to the prosthetic foot in the medial/lateral plane. Also, the curved leg is resilient to resiliently bias the upper and lower legs apart from one another so the legs are positioned in a spaced-apart relationship with respect to one another when the person's weight is off the prosthetic ankle. The resilient biasing also allows the upper and lower legs to pivot toward one another about the medial/lateral axis when the person's weight is on the prosthetic ankle at heel strike. As a result, the prosthetic foot falls flat on the ground soon after heel strike. A limit strap coupled between the upper and lower legs limits rotation of the upper and lower legs away from each other about the medial/lateral axis so the flexure characteristics experienced by an amputee during step-off are substantially determined by the flexure characteristics of the toe portion of the prosthetic foot.

1 Claim, 7 Drawing Sheets

PROSTHETIC ANKLE AND WALKING SYSTEM

FIELD OF THE INVENTION

This invention relates in general to prosthetic devices, and in particular to prosthetic ankles.

BACKGROUND OF THE INVENTION

Figure 1:
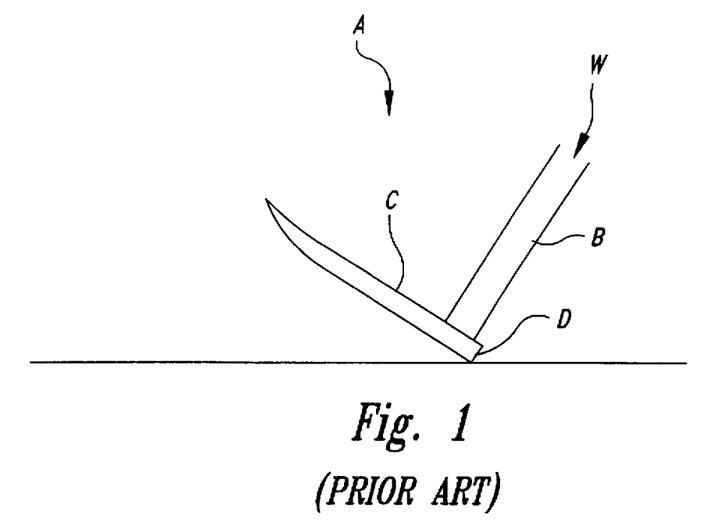
FIG. 1 is a side elevational view of a prior art walking system.

As shown in FIG. 1, leg amputees often regain significant walking capability by using a walking system A including a pylon B rigidly connected to a prosthetic foot C. Unfortunately, many of these amputees experience instability while walking. One reason for this is that the prosthetic foot C is not flat on the ground at heel strike, and does not fall flat until just prior to lift off when the amputee's weight W is coming off the prosthetic foot C. Prior to that time, the amputee's weight W is largely supported by the heel D of the prosthetic foot C. Many amputees also find these rigid walking systems uncomfortable because of a lack of cushioning at heel strike.

Figure 2:
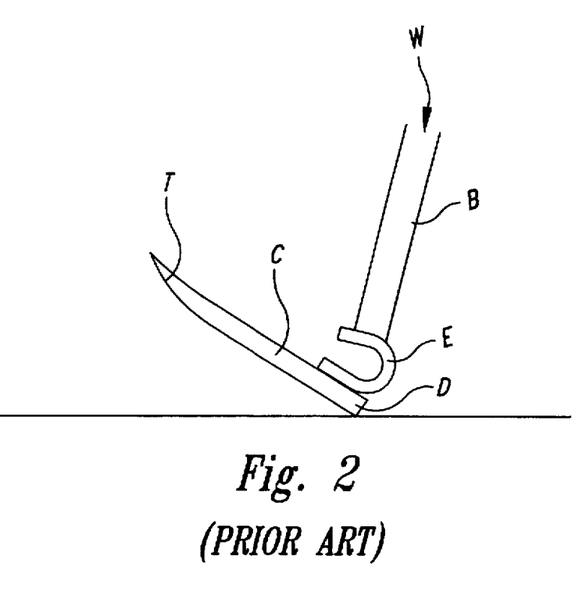
FIG. 2 is a side elevational view of the prior art walking system of FIG. 1 with a prior art resilient ankle between the pylon and prosthetic foot.

As shown in FIG. 2, prosthetists have attempted to alleviate the uncomfortable nature of rigid walking systems by inserting a resilient ankle E between the pylon B and the prosthetic foot C. Unfortunately, this has exacerbated the instability problem. The inventors have determined that the amputee's weight W at heel strike causes the toe T of the prosthetic foot C to pivot upward toward the pylon B rather than downward to the ground. As a result, the prosthetic foot C fails to fall flat for an even longer portion of the amputee's gait than with rigid walking systems.

Therefore, there is a need in the art for a walking system that places prosthetic feet flat on the ground at an earlier time during a step to provide amputees with improved stability.

SUMMARY OF THE INVENTION

An inventive walking system includes a prosthetic ankle comprising an upper leg connected to a lower end of a pylon and a lower leg connected to an upper surface of a prosthetic foot. An interconnecting member interconnects the upper and lower legs so the legs rotate about a medial/lateral axis positioned forward of the pylon. The interconnecting member resiliently biases the legs apart from one another so the legs are positioned in a spaced-apart relationship with respect to one another when the person's weight is off the prosthetic ankle. Also, the legs rotate toward one another about the medial/lateral axis when the person's weight is placed on the prosthetic ankle at heel strike, thereby allowing a toe of the prosthetic foot to rotate toward the ground at heel strike. As a result, the prosthetic foot falls flat on the ground soon after its heel strikes the ground. The inventive walking system thus provides improved stability.

DETAILED DESCRIPTION OF THE INVENTION

Figure 3:
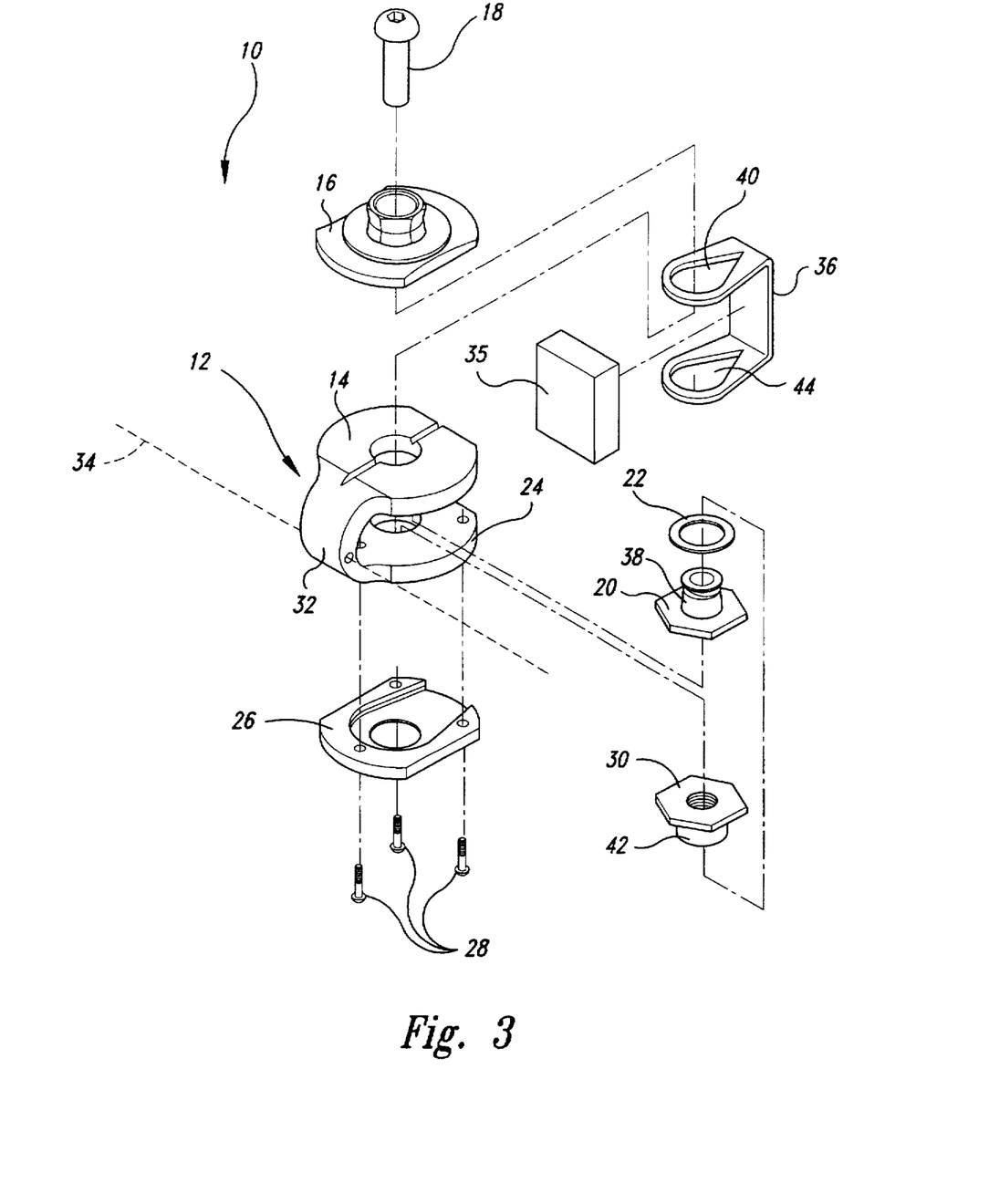
FIG. 3 is an exploded isometric view of a prosthetic ankle according to the present invention.

A preferred prosthetic ankle 10 shown in FIG. 3 includes a generally C-shaped carbon-fiber composite flexure member 12 having an upper leg 14 connected to a conventional upper attachment plate 16 with a bolt 18. The bolt 18 extends through a hole in the upper attachment plate 16 and into an upper insert nut 20 inserted into a hole in the flexure member's upper leg 14. A lock washer 22 prevents the upper insert nut 20 from turning when the bolt 18 is tight. The upper attachment plate 16 is connectable to a lower end of a conventional pylon (not shown) in a known manner. Although the present invention will be described with respect to a carbon-fiber composite flexure member, a variety of other materials will also work for purposes of this invention. For example, steel, plastic, DELRIN®, nylon and aluminum will work.

A lower leg 24 of the flexure member 12 is connected to a conventional lower attachment plate 26 with conventional fasteners, such as screws 28. The lower attachment plate 26 is connectable to an upper surface of a conventional prosthetic foot (not shown) with a bolt (not shown) extending from the prosthetic foot (not shown), through a hole in the lower attachment plate 26, and into a lower insert nut 30 inserted into a hole in the flexure member's lower leg 24. Of course, a wide variety of other mechanisms can be used to attach the prosthetic ankle 10 to a prosthetic foot, or the prosthetic ankle 10 can be integral with the prosthetic foot.

A curved leg 32 of the flexure member 12 is integral with and interconnects the flexure member's upper leg 14 and lower leg 24. The flexure member's curved leg 32 resiliently biases the flexure member's upper and lower legs 14 and 24 with respect to one another about a medial/lateral axis 34. As a result, the upper and lower legs 14 and 24 are positioned in a parallel, spaced-apart relationship when an amputee's weight is not loading the prosthetic ankle 10. Of course, other mechanisms will work as well to provide a pivotal connection between the upper and lower legs 14 and 24.

The flexure member's curved leg 32 preferably assists in making the prosthetic ankle 10 more or less rigid at toe-off. This allows the toe-off flexure characteristics experienced by an amputee using the prosthetic ankle 10 to be substantially determined by the toe portion of a prosthetic foot (not shown) attached to the prosthetic ankle, as will be described in more detail below. The prosthetic ankle 10 can do this by, for example, having a curved leg 32 constructed with the angle of the carbon fibers in the curved leg 32 varying from being parallel with the upper and lower legs 14 and 24 at the inside surface of the curved leg 32 to being perpendicular with the upper and lower legs 14 and 24 at the outside surface of the curved leg 32. This allows the flexure member's curved leg 32 to rigidly resist rotation of the flexure member's upper and lower legs 14 and 24 away from one another about the medial/lateral axis 34 past their low-load parallel position. Of course, a wide variety of other well-known carbon-fiber composite construction techniques will also work for this purpose.

Preferably, the flexure member's curved leg 32 is cut into a shape somewhat resembling a dog's bone. This 'dog-boning' helps the curved leg 32 twist more easily and allows a pylon (not shown) attached to the upper attachment plate 16 to more easily cant in the medial/lateral plane with respect to a prosthetic foot (not shown) attached to the lower attachment plate 26. The dog-boning also allows the pylon (not shown) to twist about its longitudinal axis in axial torsion with respect to the prosthetic foot (not shown). The shape, length and depth of the dog-boning can be adjusted to optimize the canting in the medial/lateral plane for a particular amputee. For example, the dog-boning on the medial side can be made deeper than the dog-boning on the lateral side so canting in the medial direction is easier than canting in the lateral direction. Also, the dog-boning can be adjusted to optimize the ability of the flexure member 12 to allow the described axial torsion. In particular, an active person, such as a golfer, might wish to optimize the axial torsion capability of the flexure member 12 so they can perform activities, such as a golf swing, which require significant axial torsion.

A resilient bias element, such as a cushion 35, can be positioned between the flexure member's upper and lower legs 14 and 24 to assist the curved leg 32 in resiliently biasing the upper and lower legs 14 and 24 with respect to each other. Of course, a wide variety of other resilient bias elements, such as air bladders, liquid bladders, and springs, will work for purposes of this invention.

A limit strap 36 brackets and couples the flexure member's upper and lower legs 14 and 24, with a shaft 38 of the upper insert nut 20 extending through an upper hole 40 in the limit strap 36 and a shaft 42 of the lower insert nut 30 extending through a lower hole 44 in the limit strap 36. The limit strap 36 assists the flexure member's curved leg 32 in rigidly limiting rotation of the flexure member's upper and lower legs 14 and 24 away from one another about the medial/lateral axis 34, and it is preferably made with non-resilient flexile Kevlar®. Of course, other flexile materials, such as nylon or a phenolic fiber material, and resilient flexile materials will also work for purposes of this invention.

Figure 4:
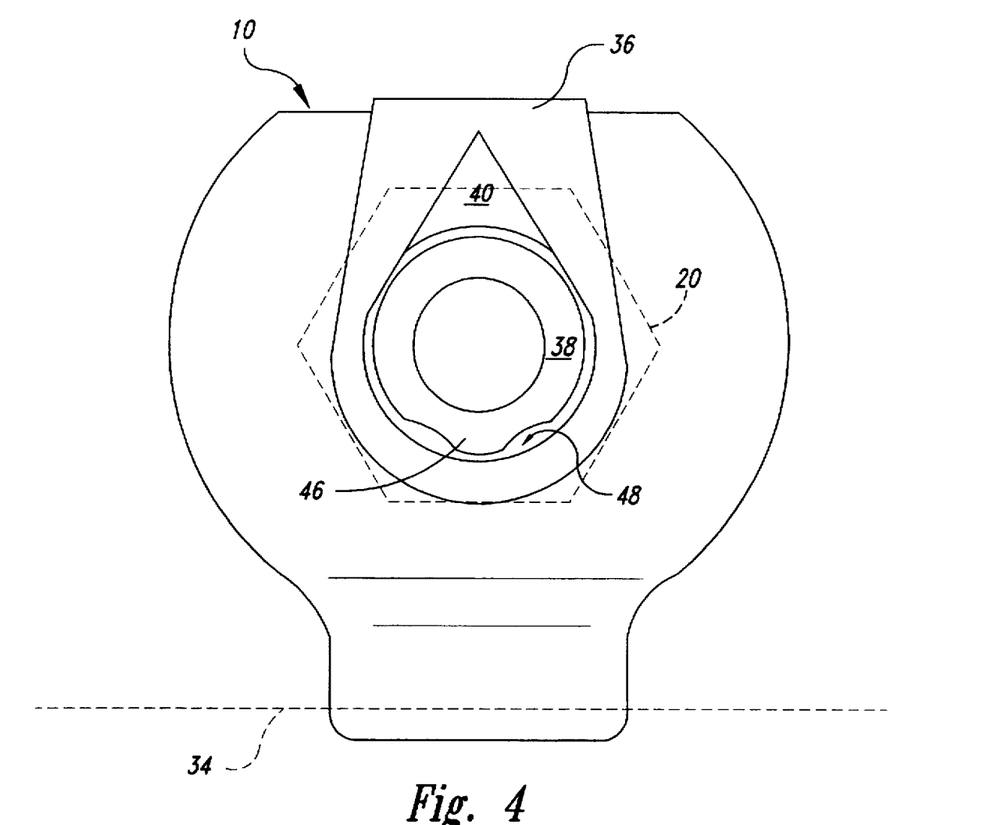
FIG. 4 is top plan view of the preferred prosthetic ankle of FIG. 3.

The limit strap 36 is shown in more detail in a top plan view of the prosthetic ankle 10 in FIG. 4. Turning the upper insert nut 20 causes a cam lobe 46 on the upper insert nut's shaft 38 to press against an interior edge 48 of the limit strap 36 and thereby tension the limit strap 36. As a result, the limit strap 36 further limits rotation of the flexure member's upper leg 14 away from the flexure member's lower leg (FIG. 3) about the medial/lateral axis 34.

Figure 5A:
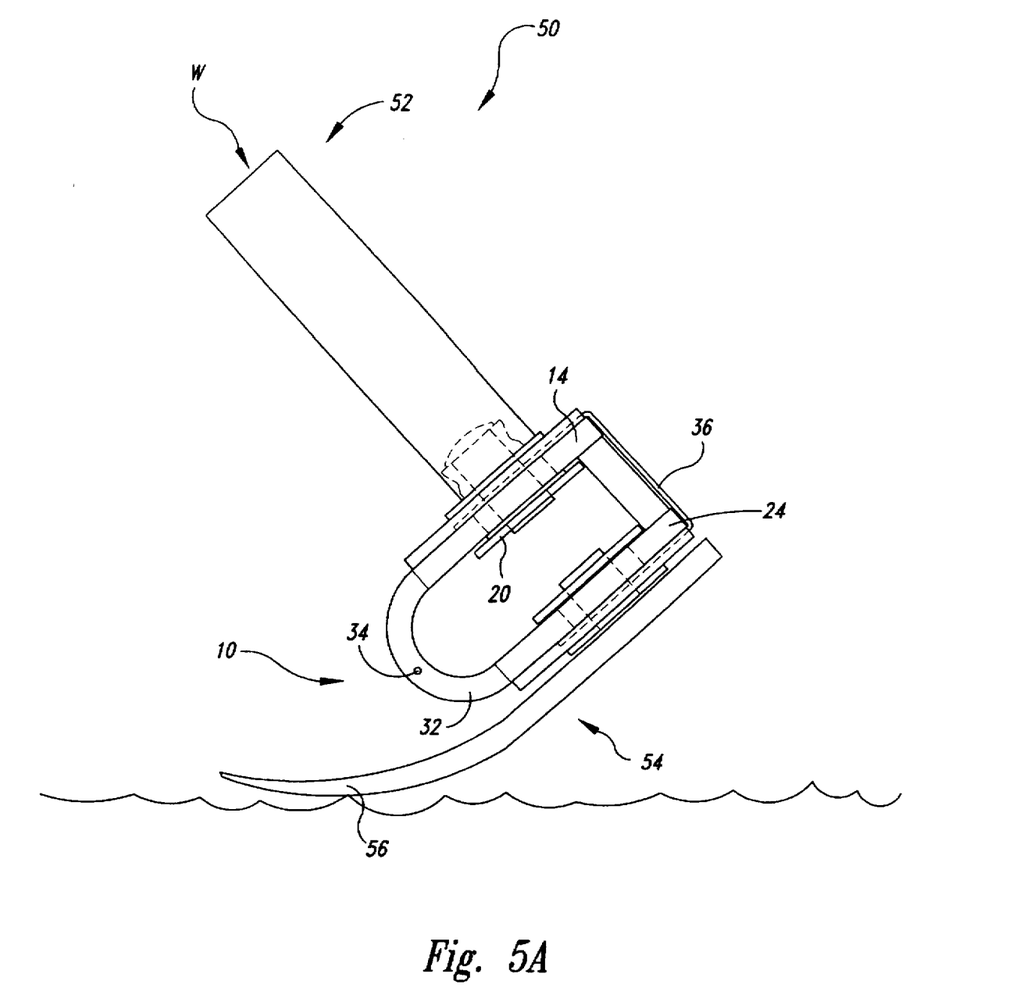
FIGS. 5A and 5B are side elevational views of a walking system including the preferred prosthetic ankle of FIG. 3.

As shown in FIG. 5A, in operation the prosthetic ankle 10 can be part of a walking system 50 including a conventional pylon 52 positioned rearwardly from the medial/lateral axis 34 and a conventional prosthetic foot 54. When the amputee is stepping off a toe portion 56 of the prosthetic foot 54 and most of the amputee's weight W is not loading the prosthetic ankle 10, the resilient curved leg 32 urges the flexure member's upper and lower legs 14 and 24 to rotate away from one another to their low-load parallel position described above.

When the flexure member's upper and lower legs 14 and 24 are at their low-load parallel position, the curved leg 32 and the limit strap 36 together rigidly limit further rotation of the upper leg 14 away from the lower leg 24 to a degree determined by the curved leg's construction and the limit strap's tension, as described above. Thus, if the upper insert nut 20 causes the limit strap 36 to be in high tension, then the flexure characteristics of the walking system 50 at toe-off are almost entirely determined by the flexure characteristics of the prosthetic foot's toe portion 56 because the prosthetic ankle 10 is substantially rigid at toe-off. If, instead, the limit strap 36 is in low tension, then the flexure characteristics of the walking system 50 at toe-off are to a greater degree determined by the flexure characteristics of the prosthetic ankle 10 because the prosthetic ankle 10 is less rigid at toe-off. This allows an amputee to conveniently adjust the flexure characteristics of the walking system 50 at toe-off for different activities such as walking, running and skiing. Of course, the limit strap 36 will also work for this purpose if the prosthetic ankle 10 opens forwardly with the pylon 52 positioned forwardly from the medial/lateral pivot axis 34.

Figure 5B:
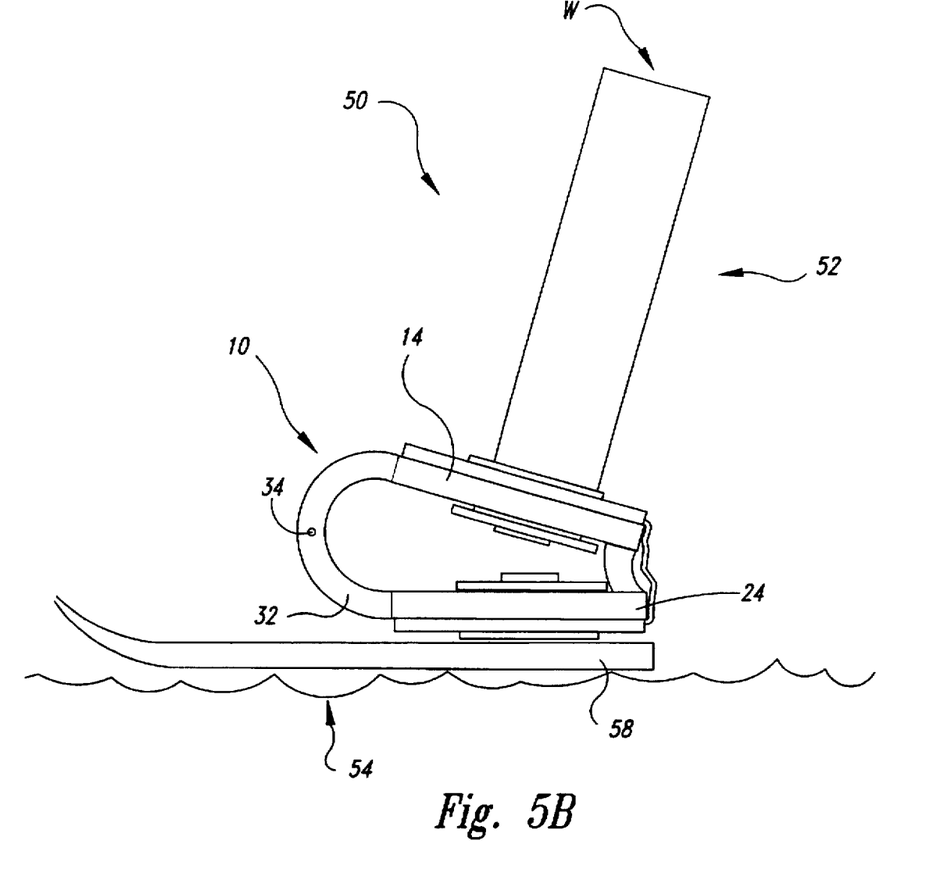

As shown in FIG. 5B, when the amputee's weight W is on the prosthetic ankle 10 and the prosthetic foot's heel 58 strikes the ground, the flexure member's curved leg 32 allows the flexure member's upper and lower legs 14 and 24 to rotate toward each other about the medial/lateral axis 34. This allows the prosthetic foot 54 to quickly fall flat on the ground when its heel 58 strikes the ground so the amputee's weight W is supported by the entire prosthetic foot 54 for most of the amputee's gait. As a result, the walking system 50 has improved stability.

Figure 6A:
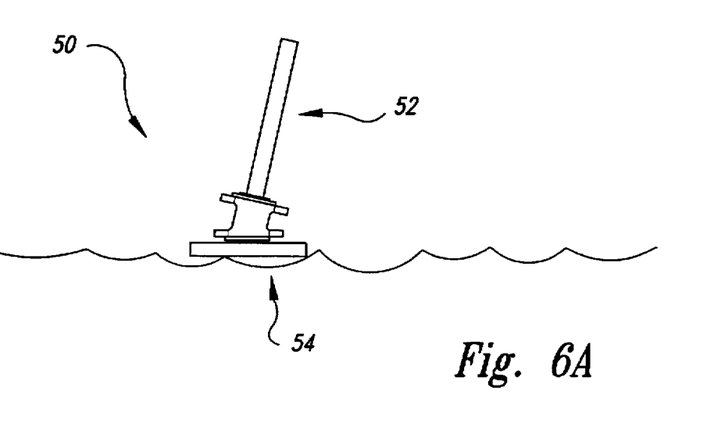
FIGS. 6A, 6B and 6C are front and side elevational views of the prosthetic ankle of FIG. 3.
Figure 6B:
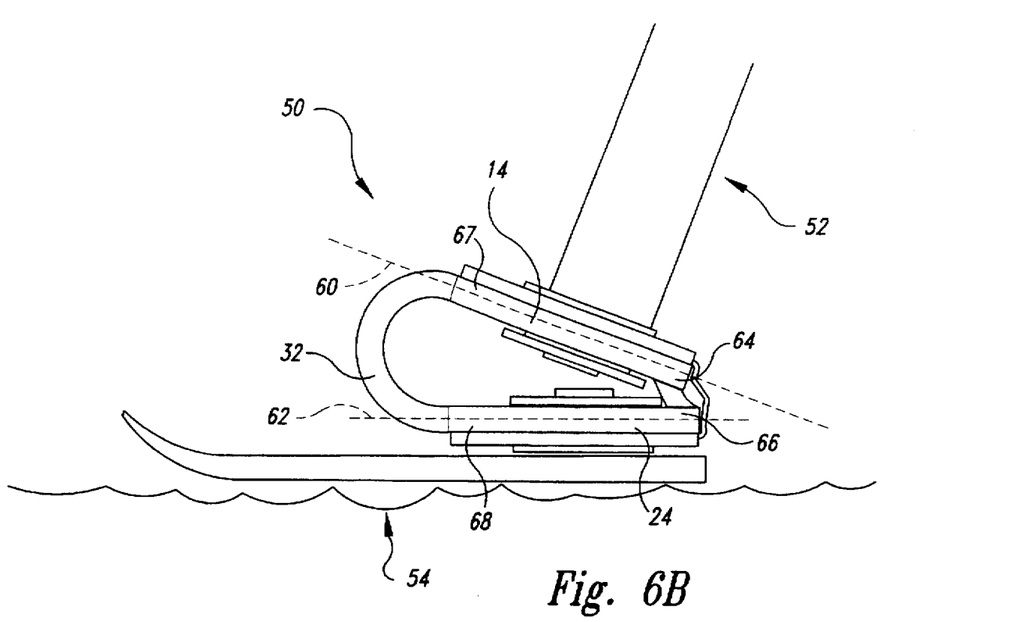
Figure 6C:
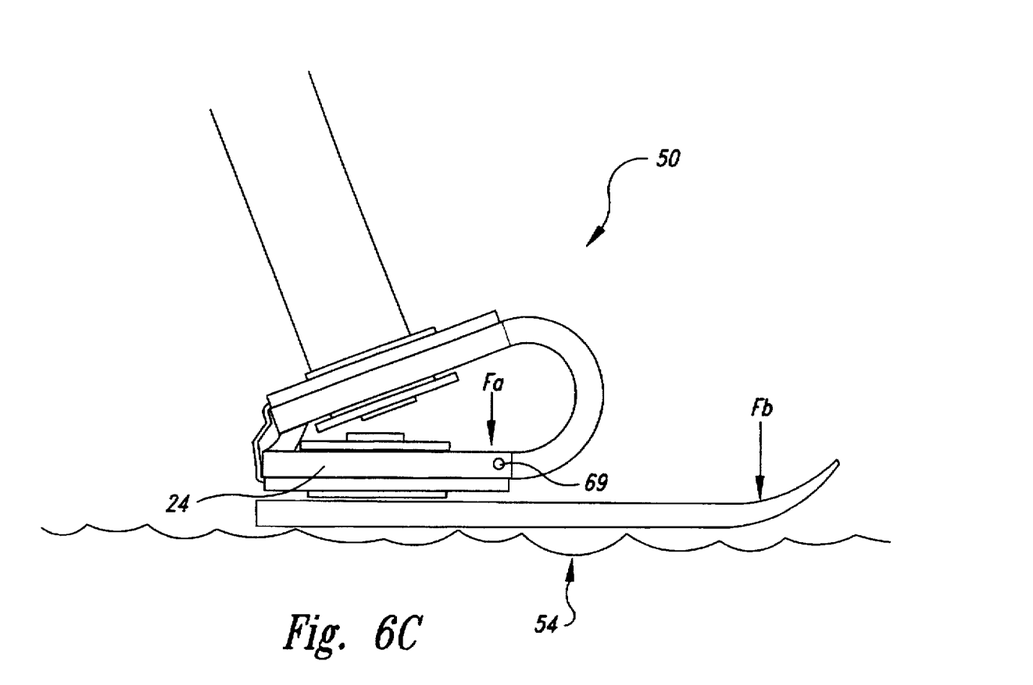

As shown in FIGS. 6A–6C, the walking system 50 also has improved stability when the prosthetic foot 54 is flat on the ground during an amputee's stride and the amputee changes direction by moving the prosthetic foot 54 in a medial or lateral direction. For example, in a front elevational view shown in FIG. 6A, an amputee's right prosthetic foot 54 is flat on the ground and the amputee moves to the amputee's left, so the pylon 52 cants in the medial direction with respect to the prosthetic foot 54. As shown in a medial side elevational view in FIG. 6B, because the pylon 52 cants in the medial direction, a twist is introduced into the upper and lower legs 14 and 24 about anterior/posterior axes 60 and 62, respectively, of the upper and lower legs 14 and 24. Because the medial posterior portions 64 and 66 of the upper and lower legs, respectively, are farther from the curved leg 32 than the medial anterior portions 67 and 68, respectively, the medial posterior portion 64 of the upper leg 14 twists downward more than the medial anterior portion 67, and the medial posterior portion 66 of the lower leg 24 twists upward more than the medial anterior portion 68. As a result, the lateral anterior portion 69 of the lower leg 24, as shown in a lateral side elevational view in FIG. 6C, is forced to twist downward with a force $F_a$. Because the lower leg 24 is connected to the prosthetic foot 54, the downward force $F_a$ on the lateral anterior portion 69 of the lower leg 24 causes a corresponding downward force $F_b$ on the lateral toes of the prosthetic foot 54. As a result, the prosthetic foot 54 "digs in" and thus is more stable when the amputee moves in the medial direction. Of course, the prosthetic foot 54 also "digs in" as necessary if the amputee moves in the lateral direction, or if the prosthetic foot 54 is the amputee's left foot.

Figure 7A:
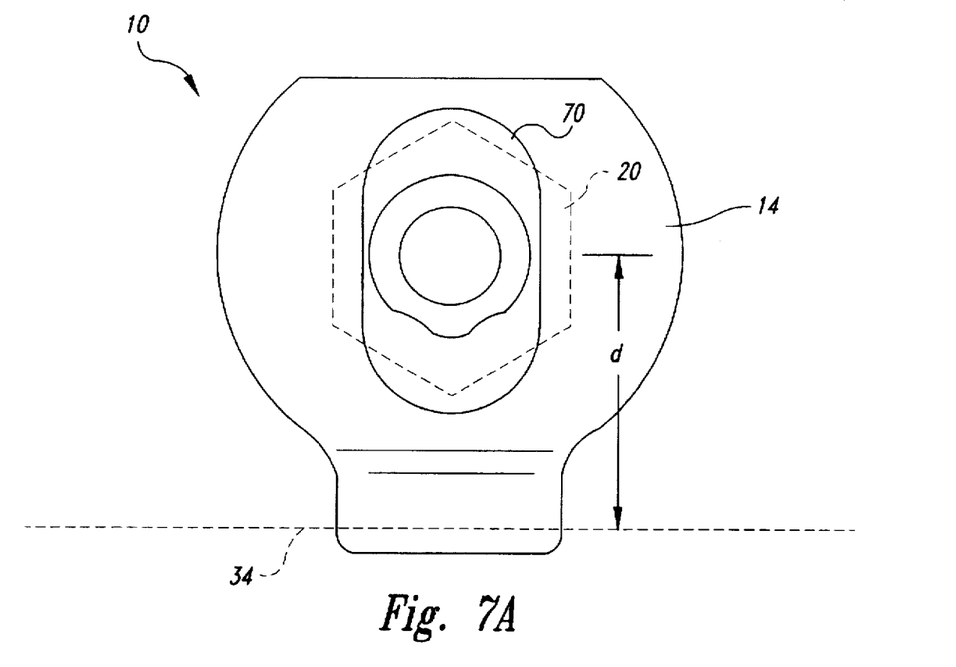
FIGS. 7A and 7B are top plan views of alternative versions of the prosthetic ankle of FIG. 3.
Figure 7B:
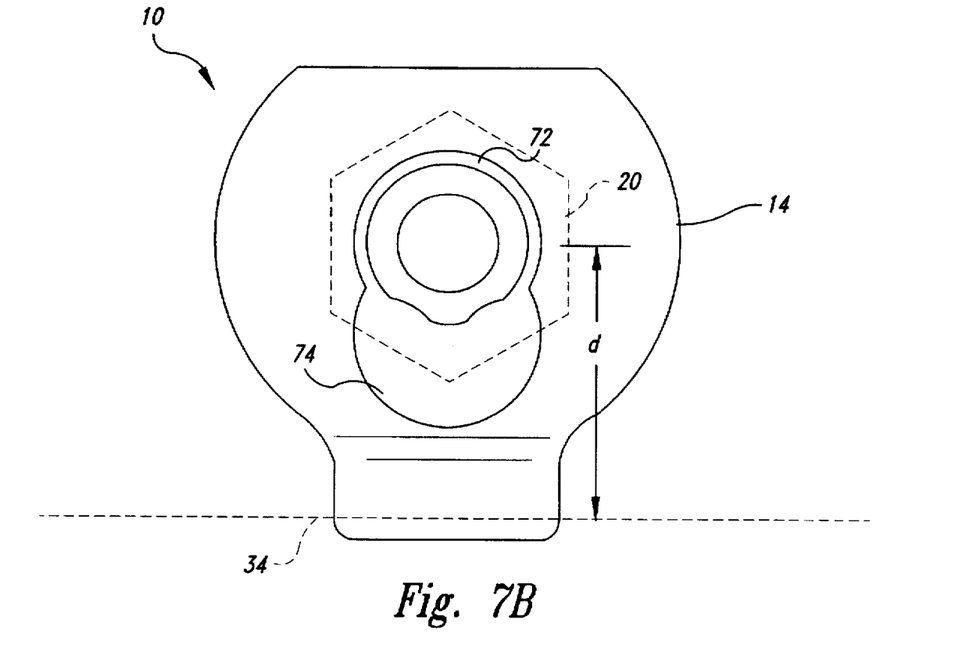

In an alternative version of the prosthetic ankle 10 shown in a top plan view in FIG. 7A, the upper insert nut 20 is inserted into a slotted hole 70 in the upper leg 14. This allows an amputee to conveniently adjust the torque arm distance d between the medial/lateral pivot axis 34 and the axes of the upper insert nut 20 and the pylon 52 (FIG. 5A). This ability to adjust the torque arm distance d allows the amputee to adjust the flexure characteristics of the prosthetic ankle 10 to suit his or her needs. Similarly, in another alternative version of the prosthetic ankle 10 shown in FIG. 7B, the upper insert nut 20 is inserted into a hole 72 in the upper leg 14 which is one of several holes 72 and 74. By selecting one of the several holes 72 and 74 for the upper insert nut 20, the amputee can adjust the torque arm distance d between the medial/lateral pivot axis 34 and the axes of the upper insert nut 20 and the pylon 52 (FIG. 5A). Thus, the user can conveniently adjust the flexure characteristics of the prosthetic ankle 10 to suit his or her needs. Although the holes 72 and 74 are shown in FIG. 7B as being partially joined, they could of course be separated by a portion of the upper leg 14.

Although the present invention has been described with reference to a preferred embodiment, the invention is not limited to this preferred embodiment. Rather, the invention is limited only by the appended claims, which include within their scope all equivalent devices or methods which operate according to the principles of the invention as described.

We claim:

1. A prosthetic ankle for use between a pylon and a prosthetic foot to support a person's weight on the ground, the prosthetic ankle comprising:

an upper leg adapted for connecting to a lower end of the pylon, the upper leg having a hole through it in substantial alignment with a longitudinal axis of the pylon;

a lower leg adapted for connecting to the upper surface of the prosthetic foot in a manner in which the lower leg is substantially prevented from moving upwardly and downwardly with respect to the prosthetic foot;

an interconnecting member interconnecting the upper and lower legs so the legs rotate about a medial/lateral axis, the interconnecting member resiliently biasing the legs apart from one another about the medial/lateral axis to space front portions of the upper and lower legs apart from one another by a greater distance than rear portions of the upper and lower legs when the person's weight is placed on the prosthetic ankle at heel strike; and a limit device having a limit strap coupling the upper and lower legs to each other and a tensioning device coupled between the limit strap and one of the upper and lower legs, wherein the limit strap has a loop having an axis positioned in substantial axial alignment with the hole of the upper leg, wherein the tensioning device comprises a cylindrical insert nut inserted into the hole of the upper leg with its axis substantially coinciding with the hole of the upper leg and with an end extending through the loop of the limit strap, and wherein the insert nut has a cam lobe on its cylindrical surface pressing against an inside edge of the loop of the limit strap such that the limit strap may be tensioned to greater and lesser degrees by turning the insert nut.

* * * * *